US008696164B2

(12) United States Patent
Kalms et al.

(10) Patent No.: US 8,696,164 B2
(45) Date of Patent: Apr. 15, 2014

(54) DEVICE FOR LASER-OPTICAL GENERATION OF MECHANICAL WAVES FOR PROCESSING AND/OR EXAMINING A BODY

(75) Inventors: Michael Kalms, Delmenhorst (DE); Christoph von Kopylow, Wilstedt (DE)

(73) Assignee: Bremer Institute fur Angewasdtestrahctechnik GmbH, Bremer (DE)

( * ) Notice: Subject to any disclaimer, the term of this patent is extended or adjusted under 35 U.S.C. 154(b) by 518 days.

(21) Appl. No.: 13/016,715

(22) Filed: Jan. 28, 2011

(65) Prior Publication Data

US 2011/0188251 A1 Aug. 4, 2011

(30) Foreign Application Priority Data

Jan. 29, 2010 (DE) .......................... 10 2010 001 357

(51) Int. Cl.
*G02B 27/20* (2006.01)

(52) U.S. Cl.
USPC ............................ 362/259; 73/827; 73/150 A (58) Field of Classification Search
USPC .................................. 362/259; 73/827, 150 A
See application file for complete search history.

(56) References Cited

U.S. PATENT DOCUMENTS

| | | | |
|---|---|---|---|
| 5,608,166 A * | 3/1997 | Monchalin et al. ............. 73/657 |
| 7,509,876 B1 * | 3/2009 | Sokol et al. ..................... 73/827 |
| 2004/0108971 A1 * | 6/2004 | Waldern et al. ................... 345/8 |
| 2005/0018299 A1 | 1/2005 | Tokoyoda et al. |
| 2009/0272724 A1 | 11/2009 | Gubler et al. |
| 2009/0310127 A1 * | 12/2009 | Parks et al. ..................... 356/70 |

FOREIGN PATENT DOCUMENTS

| | | |
|---|---|---|
| DE | 196 41 653 C2 | 6/1999 |
| JP | 08-320310 | 12/1996 |

OTHER PUBLICATIONS

A. Meyer et al., "Tailoring ultrasonic beams with optoacoustic holography", vol. 4969 (2003), pp. 105-114.
A.D.W. McKie et al.: "Laser generation of narrow-band and directed ultrasound", Ultrasonics, vol. 27, Nov. 1989, pp. 323-330.
Brinksmeier et al., "Open-Loop Fast Tool Servo With Nanometer Accuracy for Diamond Machining of Diffractive Structures".
Luenemann et al., "Open-Loop nanometerstroke fast tool servo system for the generation of diffractive optical microstructures".
M. Clark et al., "Frequency control in laser ultrasound with computer generated holography", 1998, vol. 72, No. 16, pp. 1963-1965.

(Continued)

*Primary Examiner* — William Carter
(74) *Attorney, Agent, or Firm* — Arent Fox LLP (57) ABSTRACT

A device for laser-optical generation of mechanical waves for processing and/or examining a body includes a laser light source for generation of laser light and a modulator, on which a generated laser light falls and with which, from an incident laser light, a predetermined laser light intensity distribution can be generated on or in the body, in such a way that mechanical waves are excited on or in the body, with which the body is processed and/or with which, via detection of said waves, the body can be examined. According to certain aspects of the invention, the modulator is formed as a diffractive optical element wherein a height profile structure is formed on the surface of the diffractive optical element, with which the phase of the incident laser light is varied, thus generating a predetermined laser light intensity distribution.

19 Claims, 5 Drawing Sheets

(56) References Cited

OTHER PUBLICATIONS

Wagner et al., "Modulated Laser Array Sources for Generation of Narrowband and Directed Ultrasound", 1990, pp. 263-270.

Kota Chaen et al., "Display method with compensation of the spatial frequency response of a liquid crystal spatial light modulator for holographic femtosecond laser processing," Optics Communications, 280, pp. 165-172 (2007).

M. Clark et al., "Frequency control in laser ultrasound with computer generated holography". 1998, vol. 72, No. 16, pp. 1963-1965.

* cited by examiner

DEVICE FOR LASER-OPTICAL GENERATION OF MECHANICAL WAVES FOR PROCESSING AND/OR EXAMINING A BODY

CROSS-REFERENCE TO RELATED APPLICATIONS

This application claims the priority of German Application No. PI 10 2010 001 357.9-52, filed Jan. 29, 2010, the entire specifications, claims and drawings of which are incorporated herein by reference.

BACKGROUND

1. Field

The present invention relates to a device for laser-optical generation of mechanical waves for processing and/or examining a body.

2. Introduction

It is known from the prior art to excite mechanical waves and, in particular, ultrasonic waves in a body by laser light and to examine properties of the body by detection of these waves. For example, a detection laser beam is used to detect the mechanical waves and scans the surface of the body. The laser light of the detection laser beam is modulated by the mechanical waves and this modulation and hereby the mechanical waves thus can be detected interferometrically.

German Patent DE 196 41 653 describes a method for generating and detecting ultrasound in a material, this method being based on the above-described principle of excitation of mechanical waves and the detection thereof using a detection laser.

Various approaches are known from the prior art with regard to how the Gaussian beam profile of a laser beam can be suitably modified for excitation of mechanical waves in a body. U.S. Pat. No. 7,509,876 describes, for example, the use of a laser beam with an annular beam profile. Furthermore, a method in which a laser beam is modulated for the generation of ultrasound waves by a SLM (spatial light modulator) is disclosed in Tailoring Ultrasonic Beams with Optoacoustic Holography, by A. Meyer, S. Gspan, S. Bernet, M. Ritsche-Marte, in the Proceedings of the International Society for Optics and Photonics (SPIE), Volume 4969, 2003.

The devices known from the prior art for laser-optical generation of mechanical waves pose the drawback that the generation of suitable laser light intensity distributions for the excitation of mechanical waves is only possible for predetermined wavelengths and with limited accuracy.

SUMMARY

The invention, in some aspects, enables laser-optical generation of mechanical waves in a body in such a way that laser light intensity distributions, predetermined in a simple and versatile manner, can be generated for excitation of the mechanical waves.

In accordance with various aspects of the present invention, a device comprises a laser light source for generation of laser light and a modulator, on which the generated laser light falls and with which, from the incident laser light, a predetermined laser light intensity distribution can be generated on or in the body to be examined, in such a way that mechanical waves are excited on or in the body, with which the body is processed and/or with which, via detection of said waves, the body can be examined.

In accordance with various aspects of the present invention, the modulator is formed as a diffractive optical element which is configured in such a way that a height profile structure is formed on its surface, with which the phase of the incident laser light is varied or modulated, thus generating the predetermined laser light intensity distribution. The height profile structure is formed, in particular, as a discrete structure with various height levels on the surface of the diffractive optical element. A phase modulation by variation of the geometric optical path length of the incident laser radiation is achieved by the height profile structure. Diffractive optical elements are also known per se, the use of which within the scope of a device for generating mechanical waves however affords specific advantages, since freely formed laser light intensity distributions, in particular based on a hologram formed by the height profile structure, can thus be formed as a function of the body to be examined or to be processed.

In accordance with various aspects of the present invention, the diffractive optical element comprises a reflecting member and in particular a metal member, on the surface of which the height profile structure is formed, the height profile structure preferably being milled in, in particular by a diamond turning process. A 'diamond turning process' is to be understood to mean the turning of workpieces using diamond cutting tools, in particular on machine tools which are supported pneumatically or hydrostatically and operate in a highly vibration-free manner. The diamond turning process preferably uses a 'fast tool servo system', also referred to hereinafter as an FTS system, in order to control the diamond cutting tool used in order to form the height profile structure on the surface of the diffractive optical element. In accordance with some aspects, the turning process described in Open-Loop Nanometerstroke Fast Tool Servo System for the Generation of Diffractive Optical Microstructures, by B. Lunemann, R. Glabe, E. Brinksmeier, C. Falldorf, C. V. Kopylow, in ACTUATOR 08 Conference Proceedings, 9-11 Jun. 2008 (Bremen, 2008) (referred to hereinafter as "the ACTUATOR document", the entire contents and disclosure being incorporated herein by reference), and in Open Loop Fast Tool servo with nanometer Accuracy for Diamond Processing of Diffractive Structures, by E. Brinksmeier, B. Lunemann, R. Glabe, C. V. Kopylow, C. Falldorf, and C. Dankwart, in the Proceedings of the 23$^{rd}$ Association for Standardized Patient Educators (ASPE) Annual Meeting and 12$^{th}$ ICPE (Portland, 2008), (referred to hereinafter as "the ASPE document", the entire contents and disclosure being incorporated herein by reference), based on a 'nanometer FTS servos system', may be used to form the height profile structure. In this system any holograms and non-rotationally symmetrical structures can be formed in a surface in a particularly simple manner with little effort and high precision.

In accordance with various aspects of the present invention, the diffractive optical element comprises a transmitting member and in particular a glass member, on the surface of which the height profile structure is formed, preferably again by a diamond turning process. Similarly to the above-described diffractive optical element which reflects the laser radiation, the transmitting optical element can also be produced by the same diamond turning process, i.e. in particular a diamond turning process is used in which the height profile structure is formed using a diamond cutting tool controlled by a fast tool servo system. The diamond turning methods described in the ACTUATOR document and the ASPE document can again be used for production of the diffractive optical element. The use of the above-described diamond turning processes makes it possible to form any freely formed laser light intensity distributions on or in the body in a simple and highly precise manner in order to excite efficiently adapted mechanical waves.

In accordance with various aspects of the present invention, the height profile structure is formed on the surface of the diffractive optical element in such a way that the phase of the incident laser light is varied with an accuracy of 20 nm or less, in particular of 10 nm or less. Such highly precisely produced diffractive optical elements can be achieved using the diamond turning processes according to the ACTUATOR document and the ASPE document.

The device according to various aspects of the present invention can be used in combination with laser light of a wide range of wavelengths since it is possible to achieve phase variations between 0 and 2 π for any wavelength ranges as a result of the height profile of the diffractive optical element. This is made possible, in particular, by such diffractive optical elements which are produced by the diamond turning method according to the ACTUATOR document and the ASPE document. A wide range of height differences in the height profile structure, in particular even within the nanometer range, can be produced using these turning methods.

In accordance with various aspects of the present invention, the laser light source generates laser light, of which the wavelength lies between a wavelength in the ultraviolet range and a wavelength at 10 μm, in particular in the visible range or in the infrared range or in the range between 2 and 7 μm, wherein the latter range is of particular importance for efficient generation of mechanical waves in bodies. A diffractive optical element which can modulate the phase of the light between 0 and 2 π can be produced for all these frequency ranges. Height differences in the range of the half wavelength of the laser light used and in the range of a wavelength of the laser light used thus can be ensured in the diffractive optical element for the reflecting diffractive optical element and for a transmitting, diffractive optical element respectively. A phase modulation of 0 to 2 π, even for wavelengths in the range between 2 and 7 μm, cannot be achieved with conventional liquid crystal SLMs since these only enable phase modulation for the near-infrared range to a maximum of 1500 nm owing to their structure. Different lasers can be used to generate these various laser wavelengths, in particular a Nd:YAG laser, a $CO_2$ laser, a diode laser or a femto laser.

In accordance with various aspects of the present invention, in order to generate mechanical waves with various frequencies and sufficient strength, a laser light source is used which generates pulsed laser light, in particular with a pulse length between 1 and 100 nm and with a pulse energy of at least 1 mJ.

Depending on the individual application, the device according to some aspects of the present invention can generate mechanical waves in various frequency ranges, including the excitation of ultrasonic waves on or in the body.

In accordance with various aspects of the present invention, one or more further optical elements, in particular for deflecting the laser light and/or for changing the polarisation of the laser light, is/are provided in addition to the laser light source and the diffractive optical element. Such optical elements may comprise, in particular, a beam splitter, a polarisation filter, a λ/4 wavelength plate and the like.

In accordance with various aspects of the present invention, the device may be used to examine the body. Accordingly, a detection means may be provided to detect the excited mechanical waves in such a way that corresponding properties of the body can be derived from the detected mechanical waves. This detection means is preferably configured in such a way that the excited mechanical waves are detected by the modulation of a detection laser beam scattered over the surface of the body. For special examination methods the device is further configured in such a way that it is possible to exert a load on the body using a load source either before or during detection of the excited mechanical waves. The load may vary in nature. For example, a mechanical load, or possibly a thermal load, may be exerted on the body. The load may be exerted on any side of the body on which the laser light for generating the predetermined laser light intensity distribution is incident. The load may also be exerted on the side of the body opposite this side.

As a result of the, as of yet, unknown use of the above-described diffractive element in a device for generating mechanical waves, waves in particular can be generated in or on a body in the form of a material, in particular a composite material and preferably a carbon-fibre-reinforced plastics material, for the non-destructive examination of the material. This kind of wave generation and the advantages thereof are explained in detail again with reference to FIG. 10. In particular, mechanical waves for the detection of adhesive failures in the corresponding workpiece can also be excited. The invention may optionally also be used in other fields, in particular in the medical field. For example, mechanical waves can be excited in (living or dead) human or animal or plant tissues using the device.

A specific advantage of the device described above lies in that it can be produced by a simple and cost-effective production method. In such a production method the laser light source is produced and provided in a manner known per se and the diffractive optical element is generated by a diamond turning process, wherein the height profile structure of the diffractive optical element is formed during the diamond turning process, preferably with use of a fast tool servo system. This diamond turning process has already been explained in greater detail above. In particular, the diamond turning process based on the methods described in the ACTUATOR document and the ASPE document can be implemented.

The invention further relates to the use of a diffractive optical element in the above-described device for generating mechanical waves, the diffractive optical element being produced by a diamond turning process which forms the height profile structure of the diffractive optical element, preferably with use of a fast tool servo system. The diamond turning process has already been described above in detail In particular, such diffractive optical elements are used in the device according to the invention which have been produced by a diamond turning process according to the ACTUATOR document and the ASPE document.

In accordance with various aspects of the present invention, in addition to a laser light source for generating laser light, the device comprises a modulator which is now formed not as a diffractive optical element, but as a LCOS display. This modulator carries out the same tasks as the aforementioned diffractive optical elements, i.e. the generated laser light falls on the modulator and the modulator can be used to generate, from the incident laser light, a predetermined laser light intensity distribution on or in the body to be processed or examined, in such a way that mechanical waves are excited on or in the body, with which the body is processed and/or with which, by detection of said waves, the body can be examined. Many variants of LCOS displays (LCOS=liquid crystal on silicon) are known from the prior art and are characterized in that an amplitude or phase modulation is achieved by controlling the liquid crystals, the LCOS displays being reflecting in contrast to conventional SLMs, which makes it possible to arrange the electronics in such displays in a very compact manner behind the arrangement of liquid crystals.

Compared to the use of liquid crystal SLMs in a device for laser-optical generation of mechanical waves, the use of a LCOS display as a phase modulator has specific advantages. In particular, a LCOS display exhibits a very high diffraction efficacy, reflectivity and resolution, which is substantially higher than in conventional transmitting SLMs. Furthermore, the damage threshold by laser light directed onto the modulator is substantially higher than in transmitting SLMs. The aspects of the invention with a LCOS display as a modulator can be combined with any of the above-described aspects of the invention provided these aspects are not based on the configuration of the diffractive optical element.

In addition to the above-described devices according to the invention, the invention further relates to a method for laser-optical generation of mechanical waves for processing and/or examining a body with the aid of any variant of the above-described devices according to the invention. In the method, laser light is generated by the laser light source of the device and is directed onto a modulator which, from the incident laser light, generates a predetermined laser light intensity distribution on or in the body in such a way that mechanical waves are excited on or in the body, with which the body is processed and/or with which, by detection of said waves, the body is examined. This method is optionally used merely for non-medical purposes, i.e. the method optionally comprises no such variants which are used for surgical or therapeutic treatment of human or animal bodies or which constitute diagnostic methods carried out on human bodies or animal bodies.

It is understood that other aspects of the invention will become readily apparent to those skilled in the art from the following detailed description, wherein various aspects of the present invention are shown and described by way of illustration only. As will be understood, the present invention is capable of other and different variations and its several details are capable of modification in various other respects, all without departing from the scope of the invention. Accordingly, the drawings and detailed description are to be regarded as illustrative in nature and not as restrictive.

DETAILED DESCRIPTION

Figure 1:
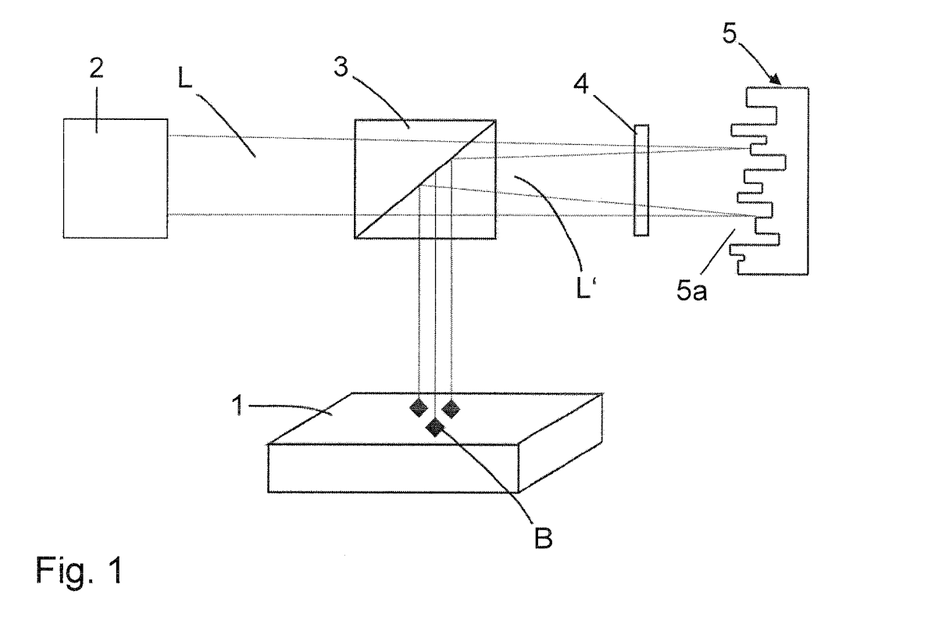
FIG. 1 illustrates a device for generating mechanical waves with use of a reflecting, diffractive optical element with a milled-in height profile, in accordance with various aspects of the present invention.

FIG. 1 shows a schematic view of a first aspects of the device according to the invention. The device in FIG. 1 excites ultrasonic waves in a body 1, wherein a laser beam L is first generated for this purpose by a laser source 2 (only indicated schematically) and is polarised in a perpendicular manner. For example, the laser source can be polarised by the intermediate arrangement of polarisation filters (not shown). The laser beam falls on a polarising beam splitter 3 which is transmissive for the direction of polarisation of the laser beam L. The laser beam L consequently passes through the beam splitter 3 and, after passing through a λ/4 wave plate, hits a diffractive optical element, also referred to as a DOE. The diffractive optical element is formed as a mirror optics and comprises a reflecting metal member, on the surface of which a height profile structure 5a is formed which is indicated merely schematically in FIG. 1. A hologram is formed by the height profile which, from the incident laser beam, generates a predetermined laser light intensity pattern by phase modulation produced by the various geometric optical path lengths of the laser light reflecting on the height profile.

The laser light L' modulated and reflected by the diffractive optical element 5 then passes again through the λ/4 wave plate 4. The polarisation of the laser light is then set in such a way that the beam splitter 3 for the laser light L' acts in a reflecting manner and the light is deflected by 90° toward the material 1. The reflected laser light generates the predetermined laser light intensity distribution on the surface of the material 1. As a result of optoacoustic interaction with the body 1, this pattern generates an ultrasonic field dependent on the energy distribution of the pattern. The waves thus excited can be body waves which move in the body, surface waves which move along the surface of the body or else 'lamb waves', where the entire body is moved. As a result of corresponding variation of the laser light intensity distribution, i.e. as a result of use of a diffractive optical element with another height profile, different types of waves can be generated depending on the individual application or the body used.

In the aspects of FIG. 1 a YAG laser with a wavelength of, for example, 1064 nm is used as the laser light source. Depending on the individual application, other YAG wavelengths may also be used. The laser beam is pulsed, wherein the pulse length may be between 1 and 100 ns depending on the individual application. The pulse length determines the wavelength spectrum of the generated ultrasonic waves. The pulse length is preferably selected in such a way that ultrasonic frequencies between 1 and 10 MHz are excited. The pulse energy is suitably adjusted as a function of the thickness of the body to be examined and is at least 1 mJ. Should the arrangement of FIG. 1 be used for examination of the body 1, the pulse energy is selected, in particular, in such a way that the ultrasonic waves excited do not destroy or change the material of the body. However, the device in FIG. 1 may also optionally be used for processing of the body 1, wherein in this instance the pulse energy is set in such a way that the structure of the material of the body is changed.

The device of FIG. 1 is characterized in that a diffractive optical element, known per se, which can be produced in a simple manner for generation of any desired laser light intensity distributions is now used for a device for laser-optical generation of mechanical waves. FIG. 2 again shows, in an enlarged perspective view, the diffractive optical element 5 used in the device of FIG. 1. This element is formed by a circular metal mirror (for example made of aluminium), on the surface of which the height profile structure 5a is produced in a diamond turning process with use of a FTS system. During this turning process, freely formed holograms can be milled into the surface of the metal member 5 using a diamond cutting tool, of which the movement is controlled by the FTS system. Based on structural data which describe the hologram, the movement of the diamond cutting tool is controlled by a control system in such a way that the hologram is formed on the surface.

Figure 2:
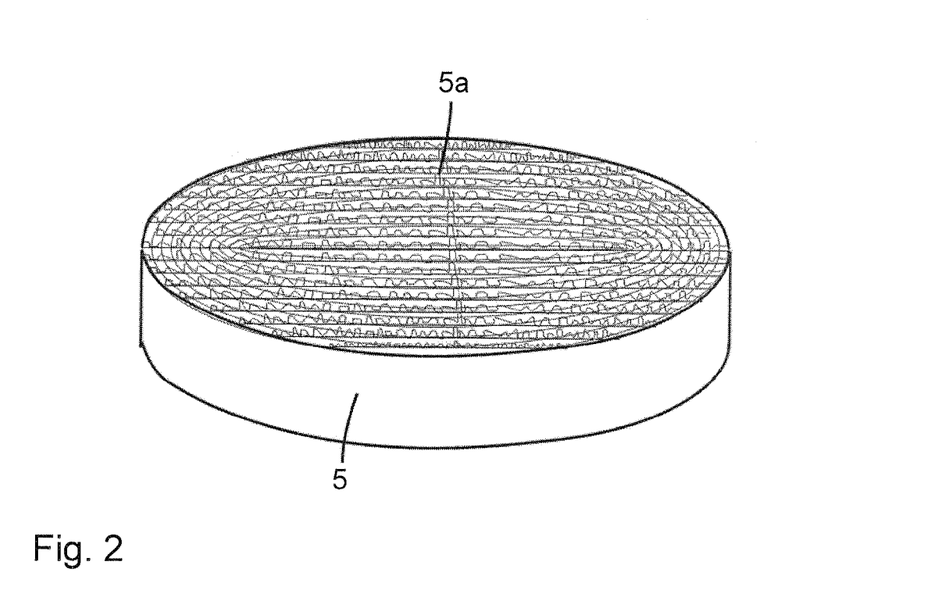
FIG. 2 is a perspective view of the diffractive optical element used in the device of FIG. 1, in accordance with various aspects of the present invention.

Diamond turning processes based on FTS systems are known per se from the prior art. In a particularly preferred aspects, a diamond turning process which is described in the ACTUATOR document and the ASPE document is used to produce the diffractive optical element 5. In this process a 'nano FTS system' with a piezoelectric actuator, for example made of lithium niobate, for controlling the diamond cutting tool is used. Structures can be milled into the surface with an accuracy of approximately 10 nm and less. Furthermore, very short stroke lengths within the nanometer range, for example of approx. 500 nm can be achieved. Depending on the individual application, it may also be possible that, instead of a nano FTS system, a different system with a longer stroke and a lesser degree of accuracy is used to carry out the diamond turning process. In particular, a micro FTS system which is known from the prior art may also optionally be used.

Diamond turning with a FTS system makes it possible to form any freely formed surfaces, even with non-rotationally symmetrical structures, i.e. depending on the individual application, any holograms can thus be impressed in the body 5 in a simple manner and any predetermined laser intensity distributions thus can be generated. The use of a diffractive optical element which has been produced by a FTS system in a diamond turning process thus provides a device for generating mechanical waves which can be adapted in a versatile manner and produced in a simple manner. Virtually any laser wavelength from the ultraviolet range to the FIR range can be used for holographic image generation as a result of the coating of the mirror 5 or as a result of the basic material of the mirror itself. This means in the device of FIG. 1, instead of a YAG laser a different laser may optionally also be used, such as a $CO_2$ laser, a diode laser or a Femto laser, depending on the individual application, wherein the wavelength of the laser can optionally be suitably varied with a 'OPO' arrangement (OPO=optical parametric oscillator).

Figure 3:
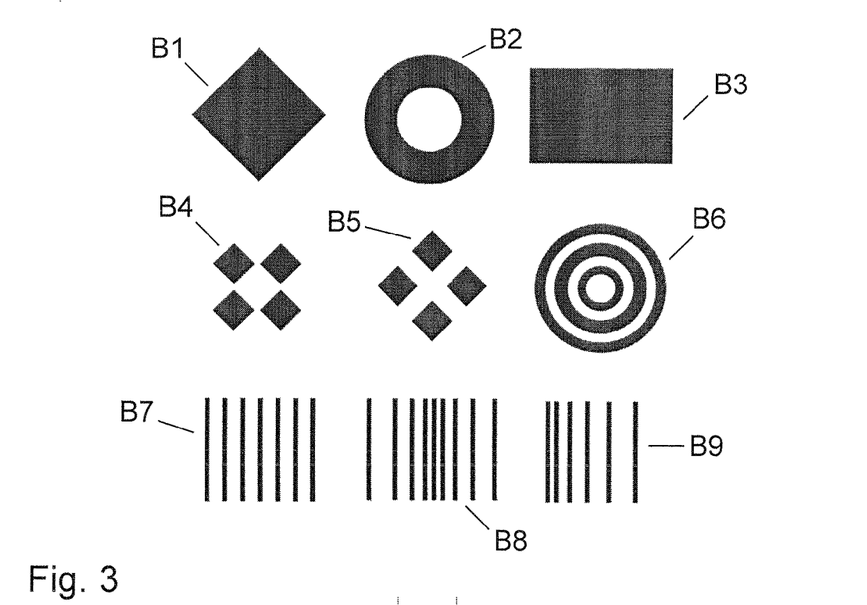
FIG. 3 shows examples of laser light intensity distributions which can be generated using the device, in accordance with various aspects of the present invention.

FIG. 3 shows some laser light intensity distributions which can be generated with a diffractive optical element according to FIG. 2. Binary laser energy distribution patterns are shown by way of example, wherein the black areas of the patterns represent points at which laser light with a constant energy distribution is arranged. The structures shown may optionally also be modified in such a way that the energy of the laser light within the structure varies, i.e. continuous laser energy distribution patterns can also be produced. FIG. 3 shows nine intensity patterns B1, B2, . . . , B9, wherein pattern B1 represents a rhombus, pattern B2 is an annular structure and pattern B3 is a rectangle. Combinations of rhombi or of a plurality of rings are also possible, as indicated by structures B4 to B6. Furthermore, it is also possible to generate strip-like structures at constant and varying distance, as indicated by structures B7 to B9. The structures shown are only exemplary and any other structures may also be generated using the above-described diamond turning process depending on the desired application.

Figure 4:
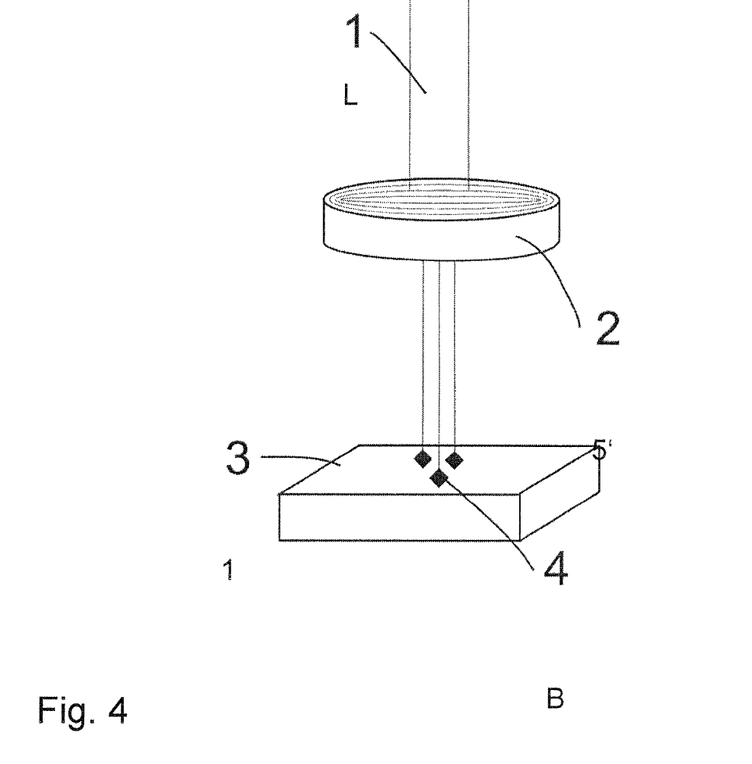
FIG. 4 illustrates a device for generating mechanical waves with a transmitting, diffractive optical element, in accordance with various aspects of the present invention.

FIG. 4 is a schematic view of another aspect of a device for laser-optical excitation of ultrasonic waves in a body to be examined 1. In contrast to the device of FIG. 1, a reflecting, diffractive optical element is now not used to generate the laser light intensity distribution, but instead a transmitting, diffractive optical element 5'. In contrast to the diffractive optical element 5, the optical element 5' consists of a material transmissive for the laser light used, for example made of silica glass. Similarly to the element 5 however, a hologram in the form of a corresponding height profile structure is again milled in on the surface of the diffractive optical element, with which hologram phase modulation is achieved based on the variation of the geometric wavelength of the incident laser light. In the aspect of FIG. 1, it is not necessary to suitably polarise the laser light or to deflect it via a beam splitter. Instead, the laser light L falls directly on the diffractive optical element 5', wherein the laser radiation is now not reflected, but passes through the optical element. Owing to the milled hologram, the predetermined laser light intensity distribution B is then formed on the body 1 behind the diffractive optical element 5', thus exciting ultrasonic waves.

In order to produce the surface structure on the diffractive optical element 5', the same methods are used which were also used to produce the diffractive optical element 5. This means that the surface of the diffractive optical element 5' can be inscribed by a diamond turning process combined with a FTS system, wherein the turning process may also be non-rotationally symmetrical. In the aspect of FIG. 4 the diffraction of the laser light is now transmissive however, so the laser beam is formed selectively behind the diffractive optical element. At the point of the optoacoustic interaction with the body 1, an ultrasonic field dependent on the laser light intensity distribution B is generated. The waves thus excited can, again, be body waves, surface waves or else lamb waves. In the aspect of FIG. 4 the same types of laser and laser wavelengths as those used in the aspect of FIG. 1 can also be used.

Figure 5:
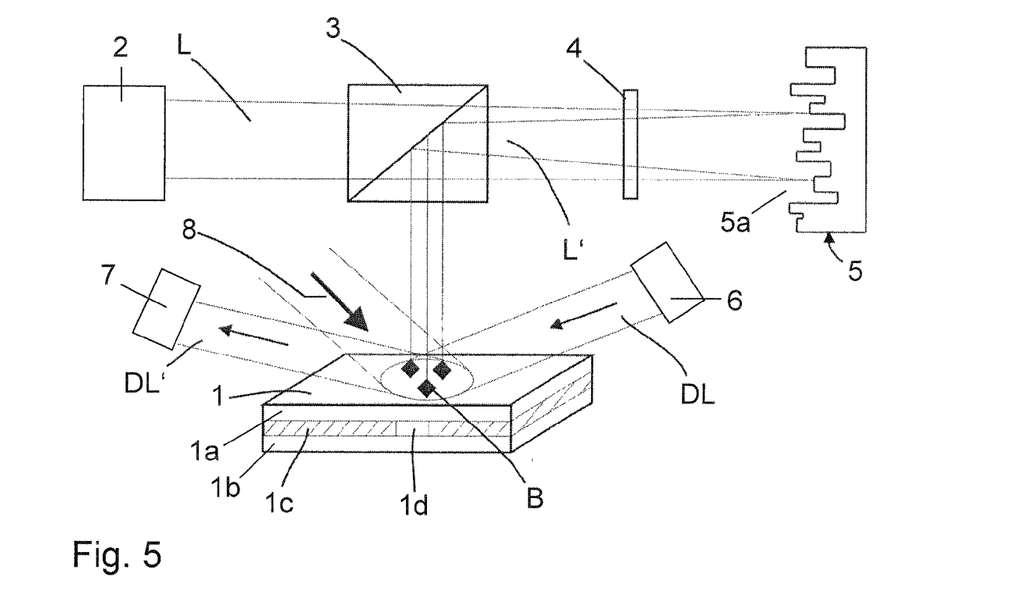
FIG. 5 illustrates a device for generating mechanical waves, in which the generated ultrasonic waves are detected by a detection laser beam with exertion of a load on the upper face of the body to be examined, in accordance with various aspects of the present invention.

FIG. 5 shows another aspect of a device according to the invention which is used to examine adhesive bonds in a composite material. The material is again denoted by the reference numeral 1. An adhesive bond 1c is arranged in the material between an upper layer 1a and a lower layer 1b, wherein an adhesive failure is present in this adhesive bond at point 1d. The bond at 1d adheres only in part, this defect being known as a 'kissing bond'. The aspect of the device shown in FIG. 5 is to detect the adhesive failure 1d. The arrangement of FIG. 5 corresponds largely to the arrangement of FIG. 1, like components in both figures being denoted by like reference numerals. In particular, a laser beam L is generated by a laser light source 2. This laser beam L passes through a beam splitter 3 and a λ/4 plate 4 and reaches the diffractive optical element 5, which is the same element as in FIG. 1. A hologram is produced by the height profile and forms on the surface of the material 1 the predetermined laser light intensity distributions B via the reflected laser beam L' deflected at the beam splitter.

As a result of the intensity pattern B on the surface of the body 1, ultrasonic waves are induced in the material which can now be detected by a suitable detection means. A detection laser beam DL is used for detection and is generated by a detection laser 6, indicated merely schematically. The detection laser beam DL falls obliquely onto the surface of the workpiece 1 and is scattered over this surface. The scattered laser beam DL' is then detected by a detector 7 which is also indicated merely schematically. The detection laser beam DL scans the surface of the body to be examined 1 for movements produced by the induced ultrasonic waves. Oscillations in the body to be examined are produced by the ultrasonic waves and modulate the detection laser light DL scattered diffusely over the body to be examined and intercepted by the detector 7. The modulation may be detected by the detector 7 in any desired manner. An interferometer in which the modulation is detected interferometrically is preferably used as a detector, for example a confocal Fabry-Perot interferometer. Any other detection techniques may also optionally be used. For example, single-beam, dual-beam or multi-beam interferometer types can be used. In particular, adaptive holographic interferometers with photorefractive crystals or with 'photo EMF detectors' can be used. In particular heterodyne aspects are used as dual-beam interferometer types. Should, depending on the individual application, only the intensity of the scattered laser light DL' be analysed, simple photodetectors can also be used.

In an aspect of FIG. 5, the adhesive failure 1d can be detected using specially excited ultrasonic fields over a previously determined laser light distribution B. In addition to kissing bonds, adhesive or cohesive bond failures can also be detected. The adhesive failures can be detected in any bodies to be examined, for example in composite fibre materials or else in bodies to be examined made of metals. Adhesive failures can optionally also be detected in bodies to be examined which consist of combinations of composite fibre materials and metals, for example in bodies to be examined formed of the material GLARE. The adhesive failures are detected in that, during scanning of the surface of the body to be examined 1, a specific modulation of detection laser light is generated which deviates from other surface regions.

In an aspect of FIG. 5, an (optional) load source is further applied obliquely to the upper face of the body to be examined 1 in the region of the holographic image B in order to effectively detect adhesive failures. This load source is indicated merely schematically by a corresponding arrow and is denoted by the reference numeral 8. The load source may be introduced before or during detection. This load source may be a mechanical load, for example in the form of vibration, microwaves, ultrasound and the like. The load may also be a thermal load, for example the introduction of radiation in the infrared range. The load may be applied at points and optionally also over the entire surface.

Figure 6:
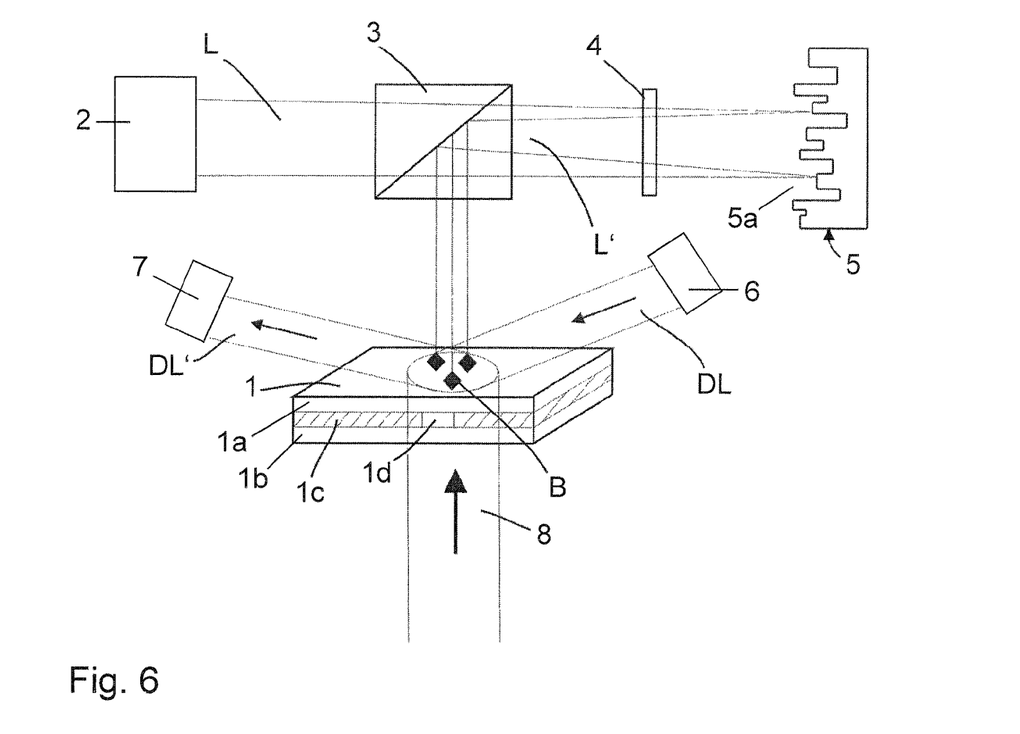
FIG. 6 illustrates a device for generating mechanical waves, in which the generated ultrasonic waves are detected by a detection laser beam with exertion of a load on the rear face of the body to be examined, in accordance with various aspects of the present invention.

FIG. 6 shows a modification to aspects of FIG. 5. Components in FIG. 6 which correspond to components in FIG. 5 are in turn denoted by like reference numerals. The beam shaping for generating the intensity pattern B corresponds to FIG. 5, so reference is made to the description of FIG. 5 in order to avoid repetitions. Similarly to FIG. 5, corresponding adhesive failures 1d are detected in FIG. 6 in a body to be examined 1 with an upper layer 1a and a lower layer 1b as well as an intermediate adhesive layer 1c. Detection is also carried out similarly to FIG. 5 using a detection laser 6 and a corresponding detector 7. A difference between FIG. 6 and aspects of FIG. 5 is that a corresponding load source 8 which, similarly to FIG. 5, may again be a mechanical or thermal load source is now applied from the rear face of the body to be examined 1. The load is exerted beneath the generated laser light intensity distribution B in the vertical direction. Similarly to FIG. 5, FIG. 6 shows a detection of ultrasonic waves by a laser beam scattered over the front face of the body to be examined. The detection may also optionally be carried out by a laser beam scattered over the rear face of the body to be examined.

Figure 7:
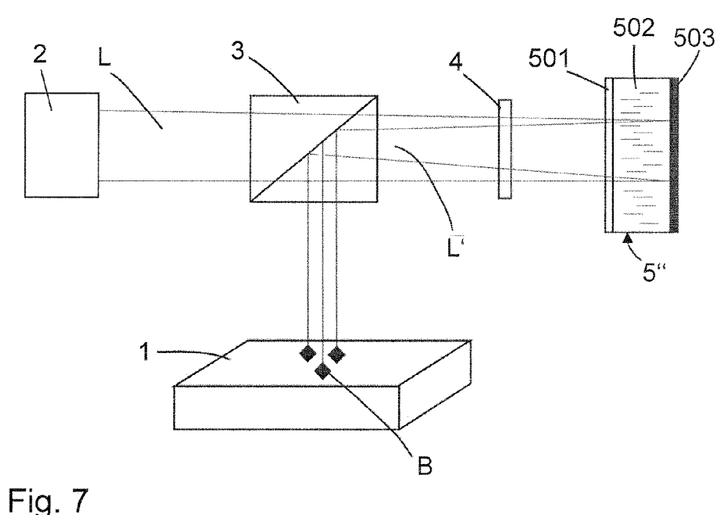
FIG. 7 is an illustration of the device of FIG. 1, wherein an LCOS display is used as a modulator instead of a diffractive optical element with a milled-in height profile, in accordance with various aspects of the present invention.
Figure 8:
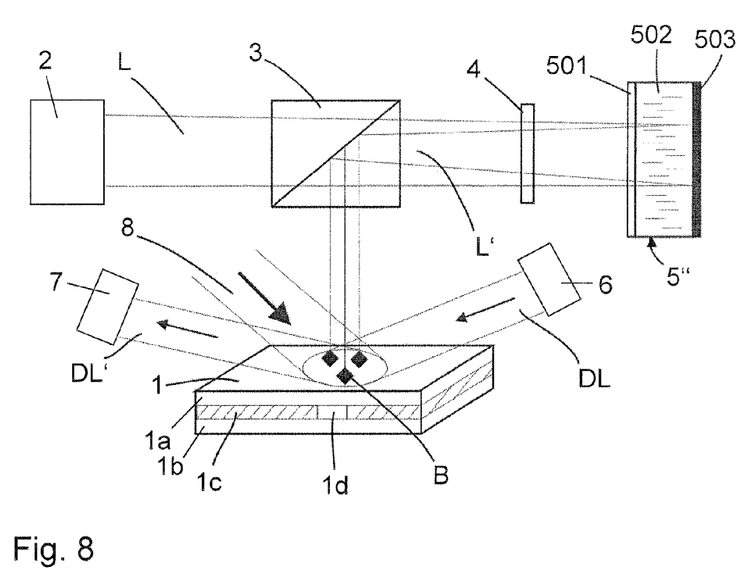
FIG. 8 is an illustration of the device of FIG. 5, wherein an LCOS display is used as a modulator instead of a diffractive optical element with a milled-in height profile, in accordance with various aspects of the present invention.
Figure 9:
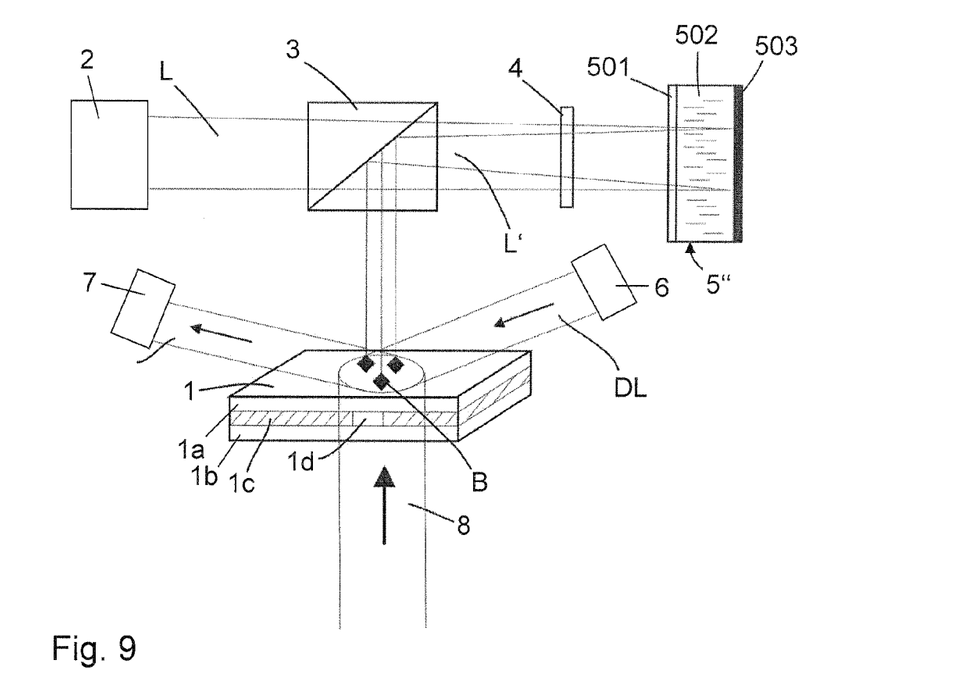
FIG. 9 is an illustration of the device of FIG. 6, wherein an LCOS display is used as a modulator instead of a diffractive optical element with a milled-in height profile, in accordance with various aspects of the present invention.

FIGS. 7 to 9 show further aspects of devices according to the invention for exciting ultrasonic waves in a body. The aspects shown in FIGS. 7 to 9 differ from the aspects described above in that a LCOS display is now used as a phase modulator instead of a diffractive optical element 5 or 5'. This display is denoted by reference numeral 5" in FIGS. 7 to 9 and comprises a front, flush glass plate 501, a rear aluminium mirror 503 or mirrored electrodes and liquid crystal elements 502 which are arranged between the glass plate 501 and the mirror 503. LCOS displays are known from the prior art and therefore will not be described in detail. In contrast to conventional LCD displays and SLMs, these displays operate in a reflecting manner and make it possible to achieve a high bulk factor since no strip conductors have to be provided between the individual liquid crystal elements. A suitable phase modulation for generation of a hologram can be generated by corresponding adjustment of the individual liquid crystal element, wherein the hologram can be suitably changed by a corresponding control of the liquid crystals depending on the individual application.

The LCOS display 5" of FIGS. 7 to 9 thus constitutes an alternative aspect of a modulator for generating a predetermined laser light intensity distribution. In particular, displays from HOLOEYE Photonics AG can be used as LCOS displays. LCOS displays form the manufacturer JVC in accordance with the D-ILA principle and from the manufacturer Colorado Microdisplay in accordance with DNLCoS technology can also be used. Furthermore, LCOS displays from the manufacturers Three-Five Systems, Micro Displays Corp., Spatialight and Aurora Systems can be used. LCOS displays were originally developed for film projectors, but can also be used for measurement purposes. The operating principle is similar to that of conventional liquid crystal SLMs. The amplitude or phase of the light is modulated in the LCOS display by the change in polarisation of the light via liquid crystals. In contrast to SLMs, the modulated light in the LCOS display is reflected.

The aspects of FIGS. 7 to 9 are characterized by the novel use of a LCOS display, known per se, in a device for exciting mechanical waves in a body to be examined. FIG. 7 corresponds to the aspects according to FIG. 1 with the only difference being that a LCOS display 5" is used instead of the diffractive optical element 5. Since the principle of excitation of mechanical waves is otherwise identical and the same reference numerals as in FIG. 1 are used, reference is made to the description of FIG. 1 in order to avoid repetitions.

FIG. 8 shows the same structure as the aspects in FIG. 5, in which an adhesive failure 1d is detected by an obliquely incident detection laser beam DL. A load source 8 is applied obliquely to the upper face of the body to be examined 1. The only difference from FIG. 5 is that a LCOS display 5" instead of a diffractive optical element 5 is now used to generate a predetermined intensity distribution B. Since the same reference numerals as in FIG. 5 are used for like components in FIG. 8, reference is made to the corresponding description of FIG. 5 in order to avoid repetitions.

FIG. 9 shows an aspects which corresponds to the aspects of FIG. 6, wherein a LCOS display 5" for generating the predetermined laser light intensity distribution B is used instead of the diffractive optical element 5. Otherwise, this aspects corresponds to the aspects of FIG. 6, i.e. induced ultrasonic waves are detected by a detection laser, a load being exerted simultaneously on the rear face of the body to be examined 1 using a load source 8. Since the same reference numerals as in FIG. 6 are used for like components in FIG. 9, reference is made to the corresponding description of FIG. 6 in order to avoid repetitions.

The above-described aspects of devices, with a diffractive optical element 5 or 5' which is produced by a diamond turning process combined with a FTS system, have a range of advantages. In particular, the diffractive optical elements 5 and 5' exhibit a high diffraction efficacy as a phase modulator of up to 90% and a high phase resolution of less than 20 nm. Furthermore, high laser outputs in the range of 10 $J/cm^2$ can be transferred by this diffractive optical element in order to excite corresponding mechanical waves. Such outputs cannot be achieved with a conventional liquid crystal SLM. The transmission of all wavelengths in the ultraviolet range, the visible range, the near-infrared range and in the far-infrared range is made possible, depending on the individual application, by the versatile configuration of the surface structure through the diamond turning process. This cannot be achieved with a conventional liquid crystal SLM since the phase modulation from 0 to 2 π is only possible for the near-infrared range of a maximum of 1500 nm. The wavelengths important for laser ultrasound excitation, in particular in the range of 2 to 3.5 μm, and the wavelengths for $CO_2$ lasers in the range of 10 μm thus cannot be generated. Compared to conventional liquid crystal SLMs, the diffractive optical elements 5 and 5' have the further advantage that they require no surrounding electronics and can be produced by the diamond turning method in a simple and cost-effective manner.

The LCOS display used in some of the aspects above also has a range of advantages within the scope of its use in a device for generation of mechanical waves. In particular, the inscribed hologram can be changed as often as desired and also very quickly using the LCOS display, i.e. a dynamic, diffractive optical element is created. Compared to conventional transmittive SLMs, the damage threshold by incident laser beams is also higher, since no strip conductors are provided between the individual liquid crystal elements. The diffraction efficacy of the LCOS display used as a phase modulator is approximately 50% and thus is higher than that in comparable display types. A reflectivity of approximately 95% can be achieved with LCOS displays, which therefore is considerably higher than that with comparable display types. Furthermore, a LCOS display makes it possible to achieve a very high resolution (similar to HDTV), i.e. high-resolution holograms can be generated for laser-optical excitation of mechanical waves. Furthermore, the structure of the LCOS display is very compact since the necessary electronics can be placed directly behind the display. Compared to the diffractive optical elements 5 and 5', the LCOS display has the advantage that corresponding holograms can be changed as often as desired and also very quickly. This makes it possible to carry out examination methods using for example quick ultrasonic alternating fields.

The device according to the invention can be used in a large number of different technical fields of application. The diffractive optical elements or the LCOS display used can generate a freely formed laser light intensity distribution which deviates from the Gaussian beam profile of a laser beam used conventionally. A non-destructive introduction of energy for ultrasound generation in various materials thus is made possible for specific applications, even with the use of a greater laser output. Selectively excited wave modes can also be implemented using a special geometric beam profile, which makes it possible to use new examination methods. In particular, the device according to the invention can optionally also be used for 'phased-array methods' in which laser light is divided into a large number of beams and is directed onto the body to be examined.

The device according to the invention can generate all known ultrasonic and sound wave shapes of any frequency by corresponding adaptation of the diffractive optical element or hologram on the LCOS display. In particular, body waves (longitudinal waves, transverse waves and all mixed forms by mode conversion) and all known surface waves (for example Rayleigh, Love and 'skimming' wave types) and all known lamb waves can be generated.

The laser wavelengths of the laser light source which are used in the device can extend from the ultraviolet range over the visible range to the near-infrared range and the far-infrared range. This applies especially to YAG wavelengths, $CO_2$ lasers, 'femto' lasers and all waves which can be generated using the OPO arrangements already mentioned above. In particular, the device according to the invention can also generate, in special aspects, wavelengths in the laser wavelength range of 2 to 4 μm and in the range of 6 to 7 μm, wherein such wavelengths can be achieved for example by the mentioned OPO arrangements. In particular, all resonance frequencies of CH bonds in matrix materials of a composite material are relevant within the scope of the device according to the invention since such composite materials thus can be examined in a suitable manner.

Depending on the individual application, the device according to the invention can generate all forms of sound waves of all frequencies. In the device according to the invention the method for generating mechanical waves can be used for any methods for examination both of technical bodies and of dead or live biological tissues. In particular, the device according to the invention may be adapted for the examination of biological tissues based on a minimally invasive examination of humans, animals or plants. For example, a laser-excited ultrasonic examination in order to detect breast cancer or other tumour-like formations can be provided with the device according to some aspects of the invention. The device may also be adapted for the examination of teeth and synthetic materials associated with dental enamel, such as fillings, crowns, bridges and the like. The device according to some aspects of the invention can also be used in methods for examination of technical objects, in particular methods based in the generation of ultrasonic waves. The examinations can be based, for example, on the pulse-echo technique and on amplitude measurement in radiography as well as on all types of propagation time measurement. The device according to some aspects of the invention is adapted, in particular, to the examination of both living trees and woods that have already been harvested.

For the purpose of non-destructive examination of material, different types of failure in different materials can be detected using the device according to some aspects of the invention. Cracks, porosities, cavity-like air pockets, material separations and adhesive failures can be particularly suitably detected. In particular, both cohesive and adhesive defects and 'kissing bond' defects can be detected using aspects of the device. The device according to some aspects of the invention is also adapted for inspection of thermoplastic components. In particular, the non-destructive examination of carbon-fibre-reinforced CETEX thermoplastic components may be carried out. Lime sand brick, concrete and any type of fibre-reinforced materials and composite materials as well as synthetic materials and renewable raw materials are also examples of materials that can be examined in a non-destructive manner.

In addition to the examination of materials and biological tissues, the device according to some aspects of the invention may also be adapted for material processing based on the laser-optically generated mechanical waves. In particular, such material processing procedures include laser beam hardening and 'laser shock deformation'. Material processing is also understood to mean all techniques for deformation of micro- and macrocomponents with laser-excited mechanical waves of any frequency.

In order to clarify the invention, a special example of application of a laser-excited ultrasound generation for the non-destructive examination of a fibre-reinforced composite material will be described hereinafter. Fibre-reinforced composite materials are to be understood, in particular, to mean fibre-reinforced plastics materials, in particular duroplastics such as CFRP materials (carbon-fibre-reinforced plastics) or other thermoplastics such as CETEX, C/PPS (CETEX carbon-fibre-reinforced polyphenyl sulphide). In accordance with some aspects of the invention, the normally Gaussian profile of the laser beam of a laser beam source is shaped by a diffractive optical element or a LCOS display (and thus adapted to the material to be inspected) in such a way that an evaluable ultrasonic amplitude can be induced in a non-destructive manner, even in the case of a material not previously accessible to laser ultrasound technology.

Laser ultrasound as a contactless measurement technique works without the use of impedance-bridging coupling means and is based on the selective introduction of laser pulse suitable for the material to be examined. In order to ensure the integrity of the object to be inspected the parameters of the laser beam generating the exciting ultrasound have to be adapted precisely to the object to be inspected. The basic principle of excitation is based on the fact that a thermoelastic source is selectively introduced into the material via the light energy of the laser pulse. The subsequent increase in volume provides a voltage field at the point where the light energy was absorbed and leads to the generation of an ultrasonic wave. The position and size of the source depend on the thermal conductivity of the material in addition to the optical penetration depth of the laser.

Figure 10:
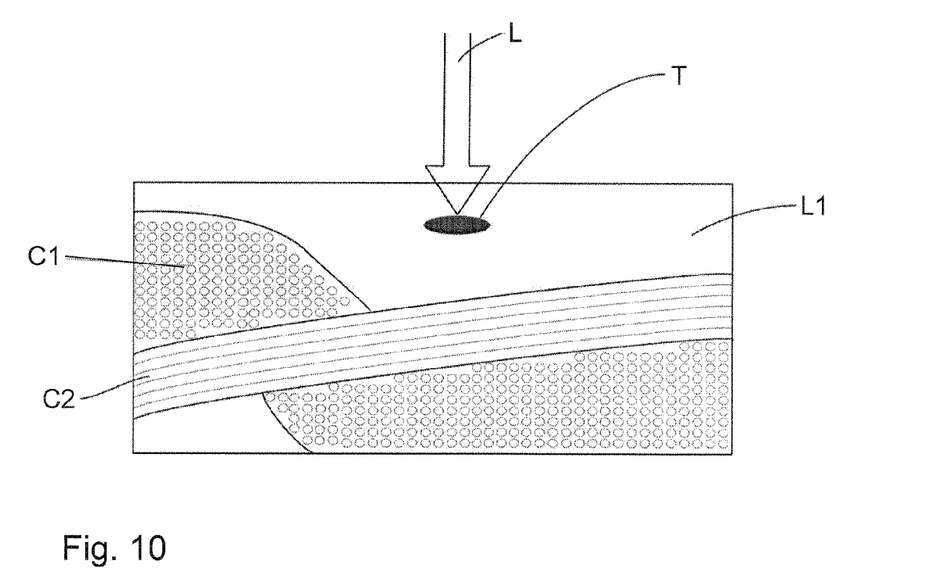
FIG. 10 is a sectional view through a carbon-fibre composite material in which ultrasonic waves are excited according to a method in accordance with various aspects of the present invention.

A two-layer structure is provided in a body to be examined made of a CFRP material, as illustrated with reference to FIG. 10. This figure is a schematic view of a section through a CFRP material. The matrix of the body to be examined, i.e. the epoxy resin, is formed by a 'Layer1-layer'. This layer is denoted in FIG. 1 by the reference numeral L1. A Layer2-layer, which represents the carbon fibres embedded in the matrix, is also provided. In FIG. 10 these fibres are denoted by reference numerals C1 and C2, wherein reference numeral C1 indicates a cross-section through a fibre and reference numeral C2 indicates a longitudinal section through a fibre. During non-destructive examination of a CFRP material of FIG. 10, a corresponding laser pulse must be placed in such a way that the maximum penetration depth lies only in the Layer1-layer. The reason for this is that a transfer of energy to the carbon fibres of the Layer2-layer is generally destructive since the rigidity of the composite only allows thermoelastic excitation via an excessive introduction of laser energy.

Depending on manufacture, the Layer1-layer thickness in a CFRP material is approximately between 10 to 50 μm. The penetration depth of a laser beam in this layer should therefore lie precisely within this range. Laser types in conventional devices for laser-induced ultrasound excitation are not suitable for the examination of the material since they have a penetration depth in epoxy resin which is much too great. In CFRP materials a $CO_2$ laser type could be used as a single laser in a conventional device for laser-induced excitation. The penetration depth in epoxy resin for such a laser type is approximately 20 to 40 μm and thus is suitable if the Layer1-layer is sufficiently thick. If this layer is not sufficiently thick, the $CO_2$ laser will also be destructive in this instance. $CO_2$ lasers with a high impulse output with simultaneous repetition rates of preferably up to 1000 Hz and more are only obtainable commercially with difficulty and therefore are very expensive. In addition, the current size of $CO_2$ lasers and the resources required for operation of conventional $CO_2$ lasers are not suitable for the industrial use in a suitable examination method. The device according to some aspects of the invention makes it possible, as a result of the use of a corresponding diffractive optical element or a LCOS display, to also use conventional commercial YAG lasers for the non-destructive examination of a CFRP material, as will be explained below.

The penetration depth of a YAG laser in epoxy resin is normally more than 100 μm. In most cases the laser energy is thus guided through the resin as far as the fibres. The energy of the laser pulse required accordingly to generate evaluable ultrasonic amplitudes is dependent on the material thickness and is normally more than 25 mJ per laser pulse. In CFRP materials this energy, alongside the conventional penetration depth of a YAG laser with a conventional Gaussian beam shape, is destructive to the fibres of the composite material. The diffractive optical elements or the LCOS display according to the invention now make it possible for the Gaussian beam profile of the YAG laser to be deformed in such a way that the introduction of energy is not destructive over suitably predetermined patterns (spatial energy distributions), though ultrasound is generated simultaneously which can be used for measurements. Examples of laser light intensity distributions that can be introduced accordingly were described previously with reference to FIG. 2. As indicated in FIG. 10, a thermoelastic source T can be generated in this manner by the laser beam L of a YAG laser in the matrix of the material and leads to the excitation of ultrasonic waves without destroying the fibres of the material in the process.

While the present invention has been described in connection with preferred aspects, it will be understood by those skilled in the art that variations and modifications of the preferred aspects described above may be made without departing from the scope of the invention. Other aspects will be apparent to those skilled in the art from a consideration of the specification or from a practice of the invention disclosed herein.

The invention claimed is:

1. A device for laser-optical generation of mechanical waves for one or more of processing or examining a body, the device comprising:
   a laser light source for generation of laser light; and
   a passive modulator on which the generated laser light falls;
   wherein based on an incident laser light, a predetermined laser light intensity distribution is generated on or in the body in such a way that mechanical waves are excited on or in the body for at least one of processing the body, via detection of said waves, or examining the body; and
   wherein the passive modulator is formed as a diffractive optical element configured with a height profile structure formed on a surface of the diffractive optical element to vary a phase of the incident laser light, thus generating the predetermined laser light intensity distribution.

2. The device according to claim 1, wherein the diffractive optical element further comprises:

a reflecting member on the surface, wherein the height profile structure is formed on the surface by a diamond turning process.

3. The device according to claim 1, wherein the diffractive optical element further comprises:
a transmitting member on the surface, wherein the height profile structure is formed on the surface by a diamond turning process.

4. The device according to claim 1, wherein the phase of the incident laser light is varied by the height profile structure with an accuracy of 20 nm or less.

5. The device according to claim 1, wherein the laser light source can generate laser light having a wavelength in the ultraviolet range at 10 micrometers, in the visible range or in the infrared range, or in a range between 2 micrometers and 7 micrometers.

6. The device according to claim 1, wherein the laser light source comprises one or more lasers selected from the group of a Nd:YAG laser, a $CO_2$ laser, a diode laser, or a femto laser.

7. The device according to claim 1, wherein the laser light source is used to generate pulsed laser light with at least one of a pulse length between 1 and 100 nanometers or a pulse energy of at least 1 millijoule.

8. The device according to claim 1, wherein the device excites ultrasonic waves on or in the body.

9. The device according to claim 1, further comprising:
one or more optical elements for at least one of deflecting the laser light or changing the polarization of the laser light.

10. The device according to claim 1, further comprising:
a detector that is configured to detect the mechanical waves.

11. The device according to claim 10, wherein the detector is configured to detect the mechanical waves by the modulation of a detection laser beam scattered over the surface of the body.

12. The device according to claim 10, wherein the device is configured to exert a load on the body using a load source either before or during detection of the mechanical waves.

13. The device according to claim 1, wherein the body comprises a material including a composite material or a carbon-fibre-reinforced plastics material, and wherein the device excites the mechanical waves in or on the material for the non-destructive examination of the material.

14. The device according to claim 13, wherein the device excites the mechanical waves for the detection of adhesive failures in the material.

15. The device according to claim 1, wherein the device excites the mechanical waves in human or animal or plant tissue.

16. A method for producing a device according to claim 1 the method comprising:
producing the diffractive optical element by a diamond turning process which forms the height profile structure of the diffractive optical element with use of a fast tool servo system.

17. The device according to claim 1, wherein the passive modulator comprises a liquid crystal on silicon (LCOS) display.

18. The device according to claim 1, wherein the phase of the incident laser light is varied by the height profile structure with an accuracy of 20 nm or less.

19. A method for laser-optical generation of mechanical waves for one or more of processing or examining a body comprising:
generating laser light with a laser light source;
directing the laser light onto a passive modulator, wherein the passive modulator uses incident laser light and generates a predetermined laser light intensity distribution on or in the body in such a way that mechanical waves are excited on or in the body, wherein the passive modulator is formed as a diffractive optical element configured with a height profile structure formed on a surface of the diffractive optical element to vary a phase of incident laser light, thus generating the predetermined laser light intensity distribution; and
at least one of processing the body with the excited mechanical waves or examining the body via the detection of said waves.

* * * * *

UNITED STATES PATENT AND TRADEMARK OFFICE
CERTIFICATE OF CORRECTION

| | | |
|---|---|---|
| PATENT NO. | : 8,696,164 B2 | Page 1 of 1 |
| APPLICATION NO. | : 13/016715 | |
| DATED | : April 15, 2014 | |
| INVENTOR(S) | : Michael Kalms et al. | |

It is certified that error appears in the above-identified patent and that said Letters Patent is hereby corrected as shown below:

On the title page item (73) should read:

(73) Bremer Institut fur angewandte Strahltechnik GmbH, Bremer (DE)

Signed and Sealed this
Twenty-fourth Day of June, 2014

Michelle K. Lee
*Deputy Director of the United States Patent and Trademark Office*

UNITED STATES PATENT AND TRADEMARK OFFICE
CERTIFICATE OF CORRECTION

PATENT NO. : 8,696,164 B2  
APPLICATION NO. : 13/016715  
DATED : April 15, 2014  
INVENTOR(S) : Michael Kalms et al.

Page 1 of 1

It is certified that error appears in the above-identified patent and that said Letters Patent is hereby corrected as shown below:

On the title page item (73) should read:

(73) Bremer Institut fur angewandte Strahltechnik GmbH, Bremen (DE)

This certificate supersedes the Certificate of Correction issued June 24, 2014.

Signed and Sealed this  
Ninth Day of September, 2014

Michelle K. Lee  
*Deputy Director of the United States Patent and Trademark Office*